(12) United States Patent
Chan et al.

(10) Patent No.: US 8,082,312 B2
(45) Date of Patent: *Dec. 20, 2011

(54) SYSTEM AND METHOD FOR COMMUNICATING OVER A NETWORK WITH A MEDICAL DEVICE

(75) Inventors: Johnny Yat Ming Chan, Arcadia, CA (US); Brent Chamblee, Aliso Viejo, CA (US)

(73) Assignee: Event Medical, Inc., San Clemente, CA (US)

( * ) Notice: Subject to any disclaimer, the term of this patent is extended or adjusted under 35 U.S.C. 154(b) by 226 days.

This patent is subject to a terminal disclaimer.

(21) Appl. No.: 12/570,584

(22) Filed: Sep. 30, 2009

(65) Prior Publication Data

US 2011/0078253 A1 Mar. 31, 2011

Related U.S. Application Data

(60) Provisional application No. 61/122,233, filed on Dec. 12, 2008.

(51) Int. Cl.
*G06F 15/16* (2006.01)
(52) U.S. Cl. ........ 709/206; 709/202; 709/205; 709/217; 709/218; 709/230; 709/246
(58) Field of Classification Search .................. 709/202, 709/205, 206, 217, 218, 230, 246
See application file for complete search history.

(56) References Cited

U.S. PATENT DOCUMENTS

| | | | |
|---|---|---|---|
| 5,692,126 | A | 11/1997 | Templeton et al. |
| 5,778,189 | A | 7/1998 | Kimura et al. |
| 5,848,415 | A | 12/1998 | Guck |
| 6,070,196 | A | 5/2000 | Mullen |
| 6,070,798 | A | 6/2000 | Nethery |
| 6,246,677 | B1 | 6/2001 | Nap et al. |
| 6,260,021 | B1 | 7/2001 | Wong et al. |
| 6,272,468 | B1 | 8/2001 | Melrose |
| 6,304,788 | B1 | 10/2001 | Eady et al. |
| 6,389,464 | B1 | 5/2002 | Krishnamurthy et al. |
| 6,473,638 | B2 | 10/2002 | Ferek-Petric |
| 6,526,970 | B2 | 3/2003 | DeVries et al. |
| 6,539,940 | B2 | 4/2003 | Zdrojkowski et al. |
| 6,574,629 | B1 | 6/2003 | Cooke, Jr. et al. |
| 6,626,175 | B2 | 9/2003 | Jafari et al. |
| 6,635,016 | B2 | 10/2003 | Finkelshteins |

(Continued)

FOREIGN PATENT DOCUMENTS

EP 1 286 280 A1 2/2003

(Continued)

OTHER PUBLICATIONS

International Search Report and Written Opinion, International Application No. PCT/US2009/063753, filing date: Nov. 9, 2009.

*Primary Examiner* — Liangche A Wang
(74) *Attorney, Agent, or Firm* — Knobbe, Martens, Olson & Bear LLP

(57) ABSTRACT

A medical device is provided that performs a requested action. The requested action may be communicated, for example, to the medical device via email messages. After performing the requested action, a response that is dependent upon the requested action is generated. The generated response is then sent on a network from the medical device as an email message.

23 Claims, 7 Drawing Sheets

U.S. PATENT DOCUMENTS

| | | |
|---|---|---|
| 6,644,311 B1 | 11/2003 | Truitt et al. |
| 6,672,300 B1 | 1/2004 | Grant |
| 6,734,880 B2 | 5/2004 | Chang et al. |
| 6,761,165 B2 | 7/2004 | Strickland |
| 6,781,522 B2 | 8/2004 | Sleva et al. |
| 6,782,888 B1 | 8/2004 | Friberg et al. |
| 6,839,753 B2* | 1/2005 | Biondi et al. ............... 709/224 |
| 6,848,444 B2 | 2/2005 | Smith et al. |
| 6,871,211 B2 | 3/2005 | Labounty et al. |
| 6,877,511 B2 | 4/2005 | DeVries et al. |
| 6,911,916 B1 | 6/2005 | Wang et al. |
| 6,918,125 B1 | 7/2005 | Skinner et al. |
| 6,932,084 B2 | 8/2005 | Estes et al. |
| 6,943,787 B2 | 9/2005 | Webb |
| 6,947,581 B1 | 9/2005 | Patel et al. |
| 6,955,171 B1 | 10/2005 | Figley et al. |
| 6,956,572 B1 | 10/2005 | Zaleski |
| 6,962,154 B2 | 11/2005 | Krebs |
| 6,963,673 B1 | 11/2005 | Patel et al. |
| 7,007,692 B2 | 3/2006 | Aylsworth et al. |
| 7,020,868 B2 | 3/2006 | Debbins et al. |
| 7,040,318 B2 | 5/2006 | Descher et al. |
| 7,063,086 B2 | 6/2006 | Shahbazpour et al. |
| 7,077,131 B2 | 7/2006 | Hansen |
| 7,082,334 B2 | 7/2006 | Boute et al. |
| 7,127,299 B2 | 10/2006 | Nelson et al. |
| 7,127,300 B2 | 10/2006 | Mazar et al. |
| 7,134,434 B2 | 11/2006 | Truitt et al. |
| 7,152,604 B2 | 12/2006 | Hickle et al. |
| 7,188,621 B2 | 3/2007 | DeVries et al. |
| 7,201,166 B2 | 4/2007 | Blaise et al. |
| 7,207,331 B2 | 4/2007 | Mashak |
| 7,219,666 B2 | 5/2007 | Friberg et al. |
| 7,255,105 B2 | 8/2007 | Figley et al. |
| 7,264,590 B2 | 9/2007 | Casey et al. |
| 7,275,540 B2 | 10/2007 | Bolam et al. |
| 7,305,988 B2 | 12/2007 | Acker et al. |
| 7,319,386 B2 | 1/2008 | Collins, Jr. et al. |
| 7,320,321 B2 | 1/2008 | Pranger et al. |
| 7,327,705 B2 | 2/2008 | Fletcher et al. |
| 7,331,343 B2 | 2/2008 | Schmidt et al. |
| 7,334,578 B2 | 2/2008 | Biondi et al. |
| 7,349,947 B1 | 3/2008 | Slage et al. |
| 7,382,247 B2 | 6/2008 | Welch et al. |
| 7,400,257 B2 | 7/2008 | Rivas |
| 7,408,439 B2 | 8/2008 | Wang et al. |
| 7,430,608 B2 | 9/2008 | Noonan et al. |
| 7,448,381 B2 | 11/2008 | Sasaki et al. |
| 7,448,382 B1 | 11/2008 | Alexander et al. |
| 7,468,032 B2 | 12/2008 | Stahmann et al. |
| 7,515,043 B2 | 4/2009 | Welch et al. |
| 7,515,044 B2 | 4/2009 | Welch et al. |
| 7,706,820 B2 | 4/2010 | Yamaki |
| 7,734,756 B2 | 6/2010 | Linderman |
| 7,840,694 B2 | 11/2010 | Yamaki |
| 7,844,657 B2 | 11/2010 | Novak |
| 7,849,140 B2 | 12/2010 | Abdel-Aziz et al. |
| 2002/0035638 A1 | 3/2002 | Gendron et al. |
| 2002/0116637 A1 | 8/2002 | Deitsch et al. |
| 2002/0120676 A1* | 8/2002 | Biondi et al. ............... 709/203 |
| 2002/0133061 A1* | 9/2002 | Manetta ............... 600/300 |
| 2003/0037261 A1* | 2/2003 | Meffert et al. ............... 713/201 |
| 2003/0107487 A1 | 6/2003 | Korman et al. |
| 2004/0054775 A1 | 3/2004 | Poliac et al. |
| 2004/0078226 A1 | 4/2004 | Becker et al. |
| 2004/0210664 A1 | 10/2004 | Prendergast |
| 2005/0080322 A1 | 4/2005 | Korman |
| 2005/0177312 A1 | 8/2005 | Guerrant et al. |
| 2005/0188083 A1* | 8/2005 | Biondi et al. ............... 709/224 |
| 2005/0192844 A1* | 9/2005 | Esler et al. ............... 705/3 |
| 2005/0257257 A1 | 11/2005 | O'Connor et al. |
| 2006/0013458 A1 | 1/2006 | Debbins et al. |
| 2006/0047538 A1 | 3/2006 | Condurso et al. |
| 2006/0052842 A1 | 3/2006 | Hess et al. |
| 2006/0154642 A1 | 7/2006 | Scannell |
| 2006/0173719 A1 | 8/2006 | Kuhn et al. |
| 2006/0235280 A1 | 10/2006 | Vonk et al. |
| 2006/0242159 A1 | 10/2006 | Bishop et al. |
| 2007/0015973 A1 | 1/2007 | Nanikashvili |
| 2007/0044799 A1 | 3/2007 | Hete et al. |
| 2007/0062530 A1 | 3/2007 | Weismann et al. |
| 2007/0073558 A1 | 3/2007 | Hall et al. |
| 2007/0088521 A1 | 4/2007 | Shmueli et al. |
| 2007/0125377 A1 | 6/2007 | Heinonen et al. |
| 2007/0125381 A1 | 6/2007 | Mashak |
| 2007/0135866 A1 | 6/2007 | Baker et al. |
| 2007/0144516 A1 | 6/2007 | Doyle |
| 2007/0163579 A1 | 7/2007 | Li et al. |
| 2007/0185547 A1 | 8/2007 | Hoyme et al. |
| 2007/0185739 A1 | 8/2007 | Ober et al. |
| 2007/0186928 A1 | 8/2007 | Be'Eri |
| 2007/0191912 A1 | 8/2007 | Fischer et al. |
| 2007/0193579 A1 | 8/2007 | Duquette et al. |
| 2007/0197881 A1 | 8/2007 | Wolf et al. |
| 2007/0215154 A1 | 9/2007 | Borrello |
| 2007/0227540 A1 | 10/2007 | Ljungberg et al. |
| 2007/0240718 A1 | 10/2007 | Daly |
| 2007/0253380 A1 | 11/2007 | Jollota et al. |
| 2007/0254593 A1 | 11/2007 | Jollota et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0299326 A1 | 12/2007 | Brown |
| 2007/0299480 A1 | 12/2007 | Hill |
| 2008/0004904 A1 | 1/2008 | Tran |
| 2008/0005054 A1 | 1/2008 | Kurian et al. |
| 2008/0011302 A1 | 1/2008 | Bassin |
| 2008/0019393 A1 | 1/2008 | Yamaki |
| 2008/0051667 A1 | 2/2008 | Goldreich |
| 2008/0058884 A1 | 3/2008 | Matos |
| 2008/0059228 A1 | 3/2008 | Bossie et al. |
| 2008/0071328 A1 | 3/2008 | Haubrich et al. |
| 2008/0072904 A1 | 3/2008 | Becker et al. |
| 2008/0078386 A1 | 4/2008 | Feldhahn et al. |
| 2008/0091175 A1 | 4/2008 | Frikart et al. |
| 2008/0092891 A1 | 4/2008 | Cewers |
| 2008/0094207 A1 | 4/2008 | Collins, Jr. et al. |
| 2008/0097552 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097914 A1 | 4/2008 | Dicks et al. |
| 2008/0110458 A1 | 5/2008 | Srinivasan et al. |
| 2008/0120284 A1 | 5/2008 | Profio et al. |
| 2008/0121232 A1 | 5/2008 | Cewers |
| 2008/0121233 A1 | 5/2008 | von Blumenthal et al. |
| 2008/0127975 A1 | 6/2008 | Lirsch et al. |
| 2008/0140163 A1 | 6/2008 | Keacher et al. |
| 2008/0140446 A1* | 6/2008 | Rosenfeld et al. ............... 705/2 |
| 2008/0141107 A1 | 6/2008 | Catallo et al. |
| 2008/0142013 A1 | 6/2008 | Hallett et al. |
| 2008/0142019 A1 | 6/2008 | Lewis et al. |
| 2008/0143538 A1 | 6/2008 | Young et al. |
| 2008/0154099 A1 | 6/2008 | Aspel et al. |
| 2008/0167902 A1 | 7/2008 | Baba et al. |
| 2008/0168990 A1 | 7/2008 | Cooke et al. |
| 2008/0173304 A1 | 7/2008 | Zaiser et al. |
| 2008/0190429 A1 | 8/2008 | Tatarek |
| 2008/0190431 A1 | 8/2008 | Bellefeuille |
| 2008/0196720 A1 | 8/2008 | Kollmeyer et al. |
| 2008/0210237 A1 | 9/2008 | McAuliffe et al. |
| 2008/0215360 A1 | 9/2008 | Dicks et al. |
| 2008/0216834 A1 | 9/2008 | Easley et al. |
| 2008/0221918 A1 | 9/2008 | Peterson et al. |
| 2008/0230059 A1 | 9/2008 | Mashak et al. |
| 2008/0245366 A1 | 10/2008 | Lee |
| 2008/0251077 A1 | 10/2008 | Durtschi et al. |
| 2008/0255885 A1 | 10/2008 | Eisenberger et al. |
| 2008/0264417 A1 | 10/2008 | Manigel et al. |
| 2008/0288294 A1 | 11/2008 | Eisenberger et al. |
| 2009/0072962 A1 | 3/2009 | Hitchin |
| 2009/0073991 A1 | 3/2009 | Landrum et al. |
| 2009/0112630 A1 | 4/2009 | Collins, Jr. et al. |
| 2009/0193435 A1 | 7/2009 | Yamaki |
| 2009/0234672 A1 | 9/2009 | Dicks et al. |

| | | | |
|---|---|---|---|
| 2009/0319776 A1* | 12/2009 | Burch et al. ............ 713/155 | |
| 2010/0235518 A1 | 9/2010 | Holden et al. | |
| 2011/0001605 A1 | 1/2011 | Kiani et al. | |
| 2011/0087756 A1 | 4/2011 | Biondi et al. | |

FOREIGN PATENT DOCUMENTS

| | | |
|---|---|---|
| EP | 1 414 509 B1 | 11/2008 |
| KR | 10-2005-0115541 | 12/2005 |
| WO | WO 98/24358 | 6/1998 |
| WO | WO 98/37704 A2 | 8/1998 |
| WO | WO 00/59566 A1 | 10/2000 |
| WO | WO 01/32069 A2 | 5/2001 |
| WO | WO 02/28123 A2 | 4/2002 |
| WO | WO 03/013635 A1 | 2/2003 |
| WO | WO 2005/050519 A1 | 6/2005 |
| WO | WO 2005/071895 A1 | 8/2005 |
| WO | WO 2005/076535 A1 | 8/2005 |
| WO | WO 2005/110238 A1 | 11/2005 |
| WO | WO 2005/117389 A1 | 12/2005 |
| WO | WO 2006/108304 A1 | 10/2006 |
| WO | WO 2010/068356 A2 | 6/2010 |

* cited by examiner

SYSTEM AND METHOD FOR COMMUNICATING OVER A NETWORK WITH A MEDICAL DEVICE

CROSS REFERENCE TO RELATED APPLICATIONS

This application claims the benefit of: U.S. provisional application No. 61/122,233, filed Dec. 12, 2008, the disclosures of which are hereby incorporated by reference in their entirety.

BACKGROUND

1. Field

The present disclosure relates to computer systems for communicating over a network with a medical device.

2. Description of the Related Art

The sharing of patient data between medical institutions and health care providers presents a variety of challenges. These challenges may include privacy, expense, accessibility, etc.

In 1996, President Clinton signed the Health Insurance Portability and Accountability Act (HIPAA). Among other things, this law (i) ensures the continuity of healthcare coverage for individuals changing jobs; (ii) includes a provision that impacts the management of health information; (iii) seeks to simplify the administration of health insurance; and (iv) aims to combat waste, fraud and abuse in health insurance and healthcare.

The Department of Health and Human Services has issued various regulations to implement these new requirements. These regulations impact all healthcare organizations that electronically create, store and/or transmit healthcare data. Among other things, HIPAA requires the secure storage and transmission of electronic healthcare data.

Setting up Virtual Private Networks (VPNs) or running point-to-point T1 lines can provide the necessary secure transmission of electronic healthcare data. However, VPNs and T1 lines can be cost prohibitive in many situations.

Alternatively, the so-called secure shell (SSH) technology and rsync protocol can be used to provide a suite of network connectivity tools which enable secure transmission of electronic healthcare data by creating a minimal subset of a many-to-one virtual network running over the public Internet.

In addition to the foregoing, medical institutions (e.g., hospitals) typically implement firewalls to limit outside access to their internal computer networks. Among other things, hospital firewalls will typically block outside attempts to access any medical data on their internal medical devices. One example of such a device is described in U.S. Pat. No. 7,040,318, the disclosure of which is hereby incorporated by reference. Outside access to such devices, even if they included an embedded server as described, is typically blocked by medical institutions.

Unfortunately, in many situations, it can be important for a healthcare provider to have access to the medical data on internal medical devices outside the healthcare institution. For example, it may be desirable to pass collected medical data from the hospital to a physician for analysis. In circumstances such as these, the aforementioned security systems for storing and transmitting electronic healthcare data can impede the electronic transfer of the data.

BRIEF DESCRIPTION OF THE DRAWINGS

Aspects and many of the attendant advantages of this disclosure will become more readily appreciated as the same become better understood by reference to the following detailed description, when taken in conjunction with the accompanying drawings, wherein.

DETAILED DESCRIPTION OF THE PREFERRED EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Systems, methods, and computer-readable media are disclosed for communicating over a network with, and obtaining medical data from, a medical device. More specifically, systems, methods, and computer readable media are disclosed for enabling an entity external to a medical institution that has a firewall or other network security system to communicate with a medical device in the medical institution.

For example, in one embodiment, a medical device is provided that performs a requested action. The medical device then generates a response that is dependent upon the requested action and sends the generated response to a node on a network from the medical device as an email message.

In another embodiment, a method of communicating with a medical device over a network is provided. The method comprises receiving over the network, by the medical device, a request to perform some action from a node, such as, an email server. The medical device then performs the requested action, wherein the request is received as an email. FIGS. 1-7 illustrate various exemplary embodiments of the invention in more detail.

Figure 1:
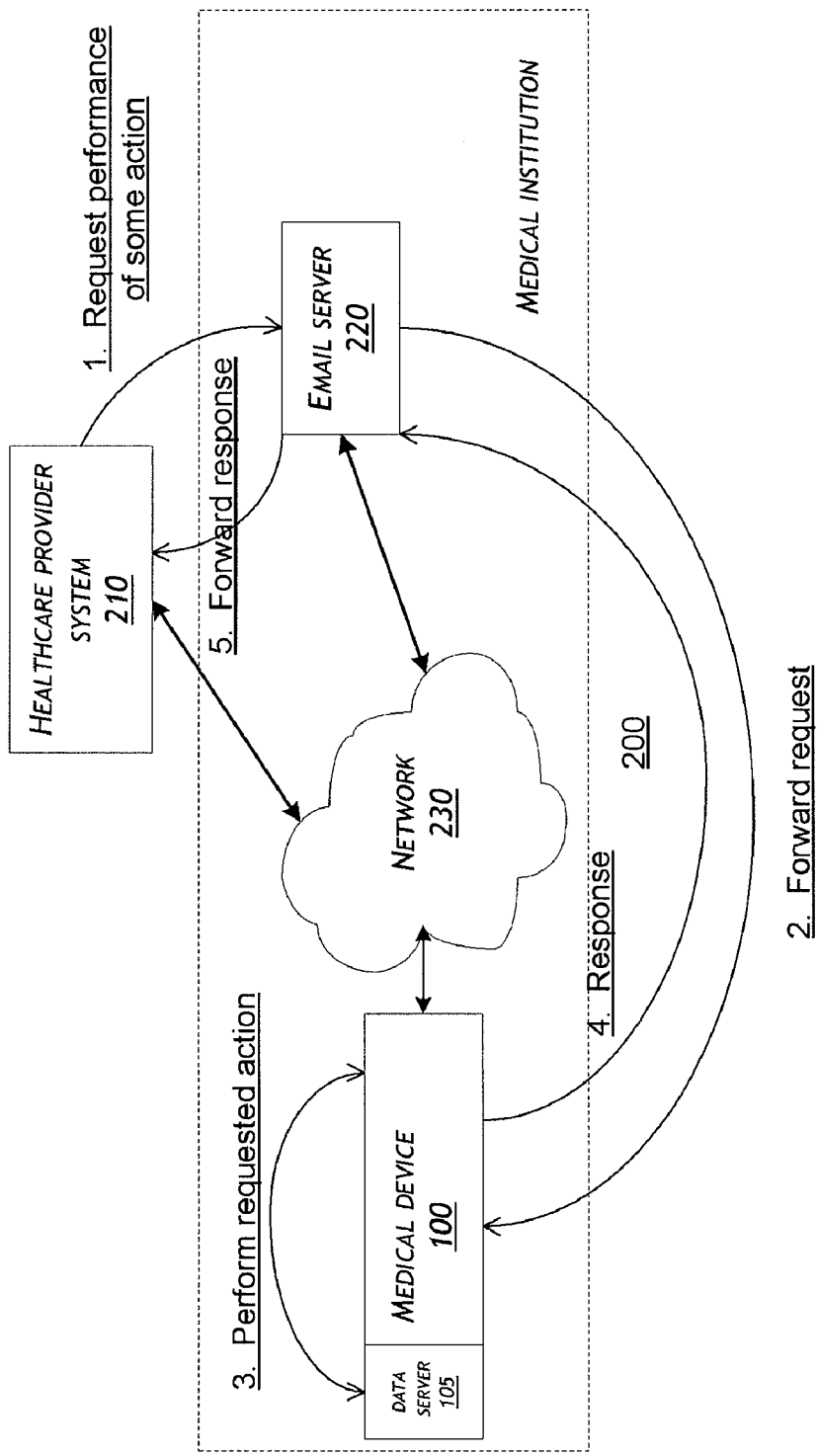
FIG. 1 is a block diagram of the system according to one embodiment.

FIG. 1 illustrates an exemplary system environment 200 for implementing embodiments of the invention. As shown in FIG. 1, system 200 may comprise multiple computer systems or machines, such as, a healthcare provider system 210 (which may be implemented as a "client"), a medical device 100 containing a data server 105, and an email server 220. These various components may be connected and communicate with one another through any suitable network 230, including the Internet. Email server 220 may be a conventional, preexisting system operated by its respective entity.

Healthcare provider system 210 may comprise any computing system used to perform tasks of some embodiments of the invention. In one embodiment, healthcare provider system 210 is maintained by a healthcare provider that desires access to medical device 100. Healthcare provider system 210 is provided a web interface such that a healthcare provider may interact with email server 220. Healthcare provider system 210 may be located at any location, such as a healthcare provider's home, office, or kiosk, etc. Additionally, one skilled in the art will appreciate that any number of healthcare provider systems may be provided to enable access to medical device 100 by healthcare providers.

Email server 220 is maintained by an entity that provides email service to employees or people associated with a medical institution. For example, email server 220 may be maintained by Google, Yahoo, etc. In a preferred embodiment, email server 220 is maintained by a hospital.

Medical device 100 is maintained by a medical institution. Medical device 100 is used by a medical institution to collect data from patients and to treat patients. Medical device 100 includes a data server 105. In a preferred embodiment, medical device 100 is a ventilator including a data server 105, such as the ventilator described in U.S. Pat. No. 7,040,318 and incorporated herein by reference. In an alternate embodiment, medical device 100 may be an implanted medical device, such as a defibrillator, pacemaker, etc., that communicates with data server 105. That is, the implanted medical device may communicate with data server 105 via a wireless link, such as an RF link. A skilled artisan will appreciate that a variety of other configurations and communication mechanisms are possible in embodiments of the present invention. Further, in a preferred embodiment, medical device 100 is associated with a unique email address.

As shown in FIG. 1, in a preferred embodiment, medical device 100 is located within a medical institution and healthcare provider 210 is located outside of the medical institution. Some embodiments of the present invention enable communication between healthcare provider 210 and medical device 100 even if the medical institution has established security measures (e.g. firewalls), as discussed above. In some embodiments of the present invention, email server 220 may be located either inside or outside the medical institution. A skilled artisan would appreciate that healthcare provider system 210 located within the medical institution would also be configured to communicate with medical device 100 in some embodiments of the present invention. A skilled artisan would also appreciate that in some embodiments of the present invention, healthcare provider system 210 would be configured to communicate with medical device 100 even if the medical institution had not established the security measures discussed above.

FIG. 1 also shows an exemplary sequence of steps (1-5) that may be performed by system environment 200 in one embodiment. The communications shown in FIG. 1 occur over one or more computer networks, such as the Internet and/or an internal network of the medical institution. First (1), healthcare provider system 210 requests the performance of some action associated with the medical device (e.g., a request for a particular item or type of data), and the request is sent to email server 220. This request may be in the form of an email. This request may be generated automatically by a special application, e.g., on input from a human operator. The type of action to be performed may be specified explicitly or implicitly in the request message. Next (2), email server 220 forwards the request to medical device 100. Then (3), medical device 100 performs the requested action and (4) sends a response to email server 220. This response may be in the form of an email reply, and may include physiologic and/or other data collected by the medical device 100 from one or more patients. Finally (5), email server 220 forwards the response to healthcare provider system 210. More detail regarding the sequence of steps will be discussed below in relation to FIGS. 4 and 5. Because the communications (1) and (5) between the medical institution and the healthcare provider system 210 can be email communications, they are not susceptible to being blocked by the medical institution's Internet firewall.

Although a single medical device is depicted in FIG. 1, many different medical devices 100 that operate as described above may be provided within the medical institution, and each may have a unique email address. In addition, multiple distinct healthcare provider entities and systems 210 may communicate with a particular medical device using the method shown in FIG. 1.

In some cases, multiple email addresses may be assigned to a given medical device 100, and the type of operation performed by the medical device 100 in response to the request may depend on the address used. For instance, an email sent to device123-data1@hospital.com may cause the device 100 to return one type of medical data, while an email sent to device123-data2@hospital.com may cause the device 100 to return another type of data.

Figure 2:
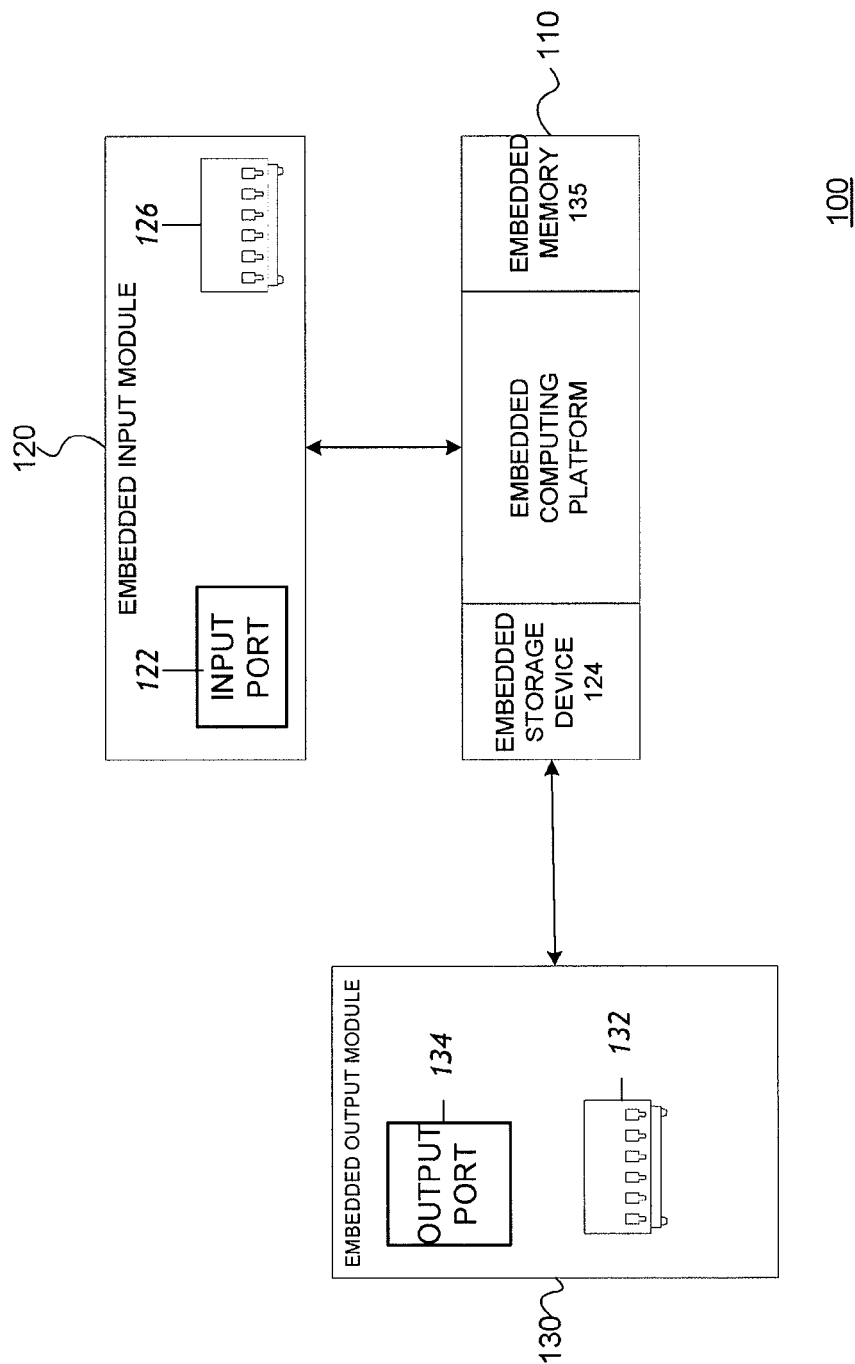
FIG. 2 illustrates the components of the medical device of FIG. 1, in accordance with one embodiment of the invention.

FIG. 2 illustrates a more detailed diagram of an exemplary medical device 100 of some embodiments of the present invention. In this example, medical device 100 facilitates the communication of medical data and in particular communication of medical data outside of medical institutions in the preferred embodiment.

As illustrated in FIG. 2, medical device 100 includes an embedded computing platform 110, an embedded input module 120, an embedded output module 130, and an embedded memory 135. Embedded computing platform 110 may be adapted to process input information received from embedded input module 120. Embedded computing platform 110 may further be adapted to provide output information to embedded output module 130.

Embedded computing platform 110 may comprise a general purpose computer (e.g., a personal computer, network computer, server, or mainframe computer) having a processor that may be selectively activated or reconfigured by a computer program to perform one or more methods of the present invention. Embedded computing platform 110 may also be implemented in a distributed network. Alternatively, embedded computing platform 110 may be specially constructed for carrying-out methods of the present invention, such as through the use of application-specific circuitry.

Embedded input module 120 may include an input port 122 and/or an embedded network interface 126. Input port 122 may be connected to patients, other medical devices, other computing devices, etc. to collect medical data that is to be communicated. Embedded network interface 126 may receive information over any type of network (not shown), such as a telephony-based network (e.g., PBX or POTS), a local area network, a wide area network, a dedicated intranet, and/or the Internet. Embedded computing platform 110 may also access data stored on embedded storage device 124. Embedded storage device 124 may include a memory, such as RAM or ROM memory, that contains instructions or data for performing one or more methods of the present invention.

Embedded output module 130 may include an output port 132 and an embedded output interface 134. Output port 132 may be connected to patients, other medical devices, other computing devices, etc. to transmit medical data, commands, requests, etc. that are received. Output port 132 may also be used to control patients, other medical devices, other computing devices, etc. Embedded output interface 134 may be used to provide relevant information to the interested parties via the Internet, email, fax, page, etc. or save the information on a computer readable medium.

Figure 3:
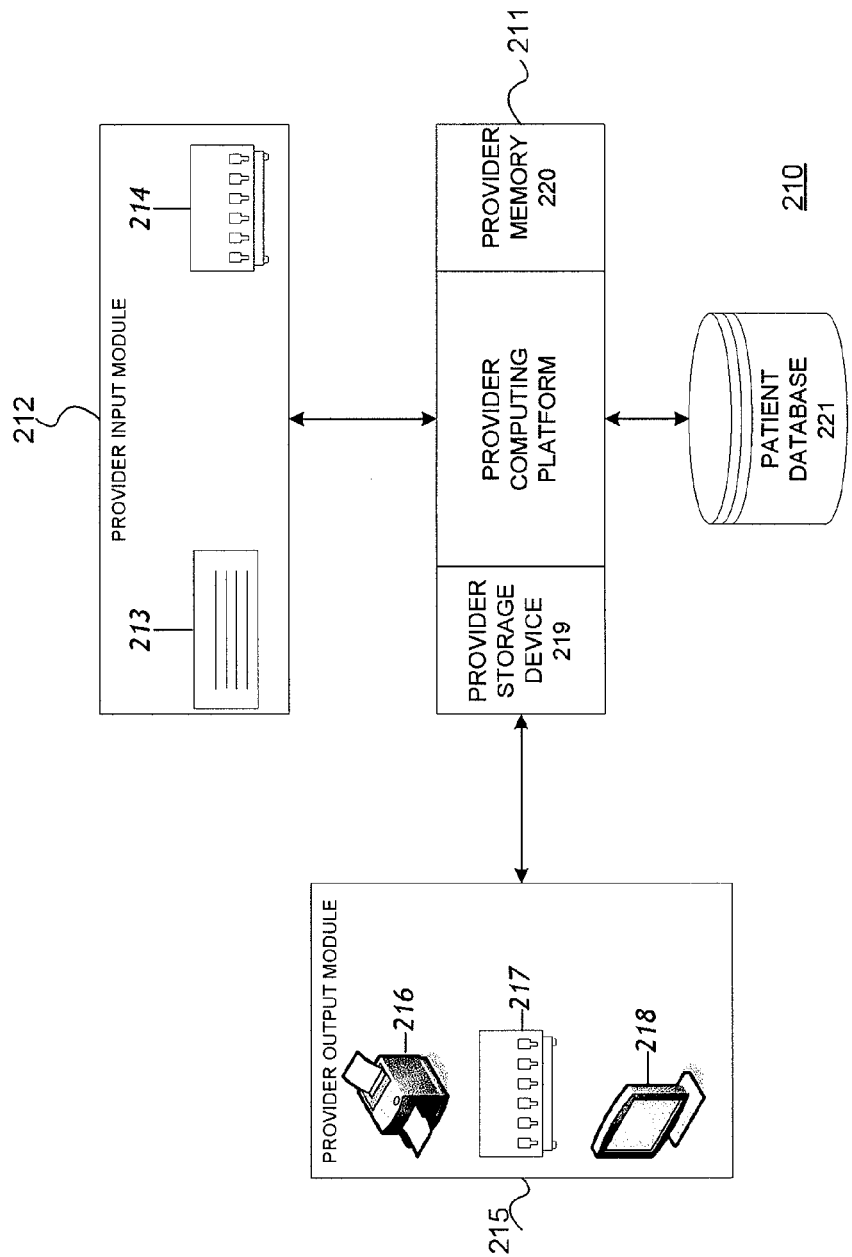
FIG. 3 illustrates the components of the healthcare provider system of FIG. 1, in accordance with one embodiment of the invention.

FIG. 3 illustrates a more detailed diagram of an exemplary healthcare provider system 210 of some embodiments of the present invention. In this example, healthcare provider system 210 facilitates the access to medical data.

As illustrated in FIG. 3, healthcare provider system 210 includes a provider computing platform 211, a provider input module 212, a provider output module 215, a provider memory 220, and a patient database 221. Provider computing platform 211 may be adapted to process input information received from provider input module 212. Provider computing platform 211 may further be adapted to provide output information to provider output module 215. Additionally, provider computing platform 211 may access information in patient database 221 for use in performing methods of the present invention.

Provider computing platform 211 may comprise a general purpose computer (e.g., a personal computer, network computer, server, or mainframe computer) having a processor that may be selectively activated or reconfigured by a computer program to perform one or more methods of the present invention. Provider computing platform 211 may also be implemented in a distributed network. Alternatively, provider computing platform 110 may be specially constructed for carrying-out methods of the present invention.

Provider input module 212 may include a provider input device 213 and/or a provider network interface 214. Provider input device 213 may be implemented using a keyboard, mouse, speech recognition device, and/or data entering devices. Provider network interface 214 may receive information over any type of network (not shown), such as a telephony-based network (e.g., PBX or POTS), a local area network, a wide area network, a dedicated intranet, and/or the Internet. Provider computing platform 212 may also access data stored on provider storage device 219. Provider storage device 219 may include a memory, such as RAM or ROM memory, that contains instructions or data for performing one or more methods of the present invention.

In accessing medical data, provider input module 212 may be used to enter or obtain medical data from medical institutions, commands to be sent to medical institutions, requests to be sent to medical institutions, etc. Such information and requests may be obtained, for example, from an employee, from provider storage device 219, and/or from another computing system via provider network interface 214. Provider computing platform 211 may store such information received from provider input module 212 in patient database 221.

As further described below, provider computing platform 211 may use the stored patient information to generate reports, alerts, and the like for healthcare providers. Provider computing platform 211 may then output the requested information via provider output module 215.

Provider output module 215 may include a printer 216, a provider output interface 217, and/or a display 218. Printer 216 may be used to provide a printout to interested parties of relevant information, such medical data collected from etc. Provider output interface 217 may be used to provide such relevant information and/or other information to the interested parties via the Internet, email, fax, page, etc. or save the information on a computer readable medium. Display 218 may be used to provide such relevant information to interested parties visually.

Patient database 221 may include patient account data and healthcare provider data. Patient account data preferably includes a record of all personal data associated with patients connected to medical device 100, such as name, address, telephone number, driver's license number, social security number, credit card account number, checking account number, etc. Healthcare provider data preferably includes records of all reports generated for the healthcare providers, alerts generated for the healthcare providers, patients associated with the healthcare providers, requests made by the healthcare providers. Healthcare provider data may also include the healthcare provider's membership identification ("ID") and password. The information to be stored in patient database 221 may be entered or obtained using provider input module 212.

Figure 4:
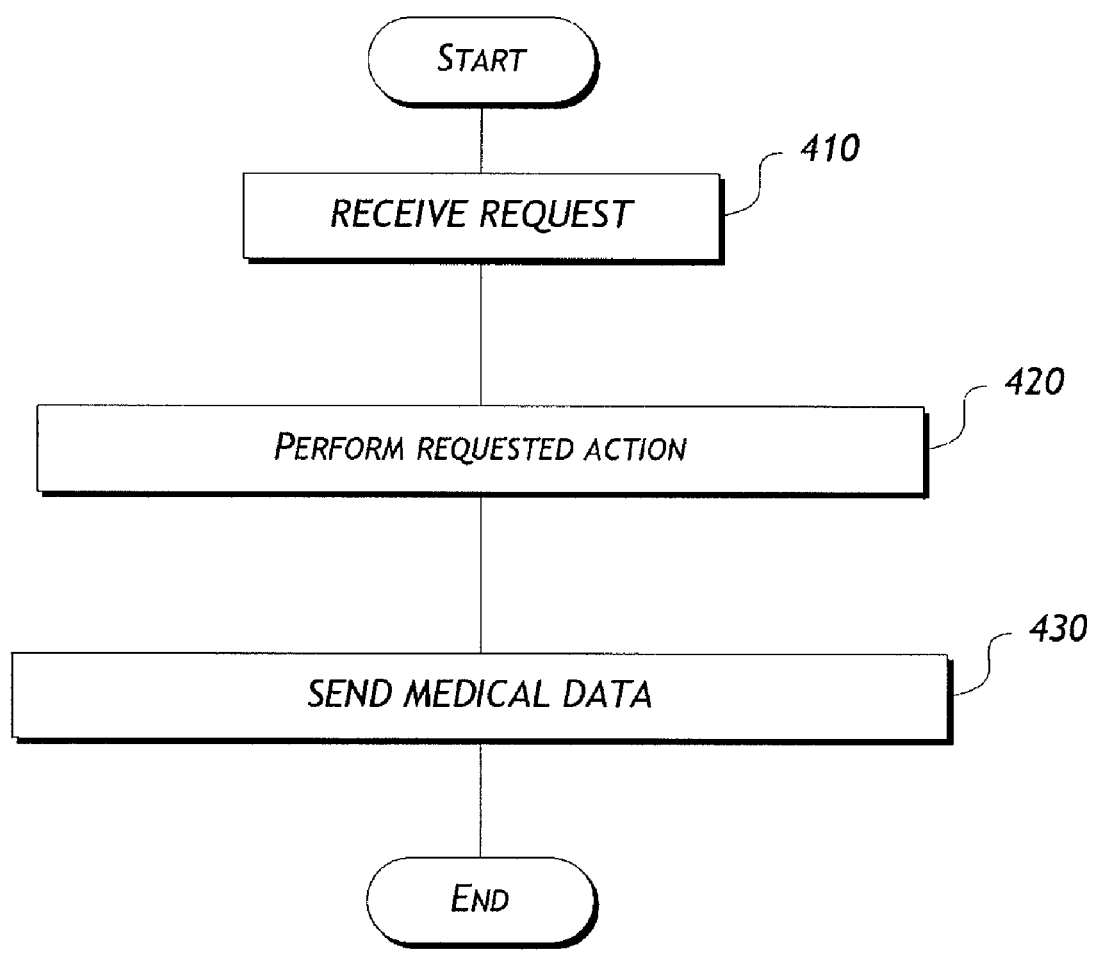
FIG. 4 illustrates a sequence of steps that may be performed by the medical device of FIG. 1, in accordance with one embodiment of the invention.

FIG. 4 illustrates a flowchart of an exemplary process for communicating medical data of some embodiments of the present invention. This process may be implemented by the medical device 100, and may be embodied in software and/or application-specific circuitry. Although the steps of the communication process are described as being performed in a particular order, one skilled in the art will appreciate that these steps may be performed in a modified or different order, or in an embodiment utilizing less than all of the steps described below. Further, one or more of the steps in FIG. 4 may be performed concurrently or in parallel.

First, embedded computing platform 110 receives a request (Step 410) generated by healthcare provider system 210. The request typically explicitly or implicitly specifies a particular action to be performed by medical device 100. In one embodiment, the request from the healthcare provider is sent to email server 220 which then sends the request to medical device 100. The request is received over network 230. In a preferred embodiment, the requests are received as emails using the POP protocol. That is, the healthcare provider sends the request to email server 220 using SMTP or IMAP protocols and then email server 220 forwards the email to the unique email address associated with medical device 100 using POP. Sending the requests as email messages may allow the communication and sending of data to medical device 100 even though the medical institution where medical device 100 exists has established a firewall. Embedded computing platform 110 may in one embodiment, periodically check or request email server 220 to send medical device 100 any emails or requests that are to be sent to medical device 100. In another embodiment, email server 220 sends emails or requests directly to medical device 100 without waiting for a request. That is, in such an embodiment, medical device 100 does not periodically request or check for emails but receives the emails directly from email server 220 as they are received. Further, a skilled artisan will appreciate that a variety of other protocols could be used in embodiments of the present invention. For example, FTP, FTPS, SSH, HTTP, HTTPS, VOIP, GPS, CDMA, GSM, etc. may be used in some embodiments of the present invention. Moreover, a skilled artisan will appreciate that the email server 220 or another intermediate system can be configured with appropriate rules to prevent the medical device 100 from receiving unwanted messages or spam. For example, an incoming email addressed to the medical device 100 can be blocked if it is not from a trusted source, and/or if the message portion is not formatted properly (e.g., does not include a valid command or authentication signature).

Next, embedded computing platform 110 performs the requested action (Step 420). As part of this step, embedded computing platform 110 may parse the received request or email and perform the action as requested. A skilled artisan will appreciate that in some embodiments of the present invention, a protocol for communicating data between medical device 100 and healthcare provider system 210 via standard email messages may be established. As such, parsing of the request would be possible based on the defined protocol using conventional methods as is known in the art. If the received request relates to collecting medical data, embedded computing platform 110 may collect the requested medical data. If the received request relates to performing some other action (i.e., set parameters on a connected device, take an image, control some valve, etc.), embedded computing platform 110 can perform the requested action.

For example, in the preferred embodiment, various settings for the ventilator may need to be configured in order for them to be administered properly. Examples of commonly required settings to control a ventilator include: Peak Inspiratory Pressure (PIP) setting-limiting the peak pressure during inspiration of air; and Positive End Expiratory Pressure (PEEP) setting-limiting the peak pressure at the end of expiration of air. Many other ventilator settings may also be controlled. In addition, some ventilators are equipped with various sensors so that a patient caregiver may monitor the condition of the patient through the ventilator. Examples of commonly monitored parameters for a ventilator include Mean Airway Pressure (MAP)—the mean pressure measured within the airway during the breathing cycle; and Tidal Volume Inspired (Tvi)—measured volume of gas inhaled by the patient during a normal breath. Many other ventilator parameters may also be monitored. As a consequence, embedded computing platform 110 of the ventilator in the preferred embodiment may perform some action requested. Exemplary actions may include, "set PIP," "get ventilator data," "get MAP," "take image," etc. A skilled artisan will appreciate that a variety of other actions are possible in embodiments of the present invention.

In an alternate embodiment, embedded computing platform 110 automatically performs some action without waiting for a request (i.e., step 410 is skipped). In this embodiment, embedded computing platform 110 can be configured to perform some action automatically at predetermined intervals (e.g., daily, weekly, monthly, etc.). A skilled artisan will appreciate that the request received in step 410 may be a request to configure embedded computing platform 110 to perform some action automatically. For example, the request could configure embedded computing platform 110 to collect specified medical data every week. In this example, after receiving the request, embedded computing platform would collect the specified medical data every week automatically without waiting for a request.

In some embodiments, embedded computing platform 110 can be configured to perform some action automatically when a triggering event occurs. For example, embedded computing platform 110 may determine that medical device 100 has malfunctioned, that some readings from the patient are abnormal, that some patient readings have crossed some predetermined thresholds, etc. When such a triggering event occurs, embedded computing platform 110 may proactively send collected medical data by email to the healthcare provider system 210, without waiting for a request. The healthcare provider system 210 may set up such triggers by sending appropriate commands to the medical device 100 by email.

In Step 430 of FIG. 4, embedded computing platform 110 sends the collected medical data via an email message. As part of this step, embedded computing platform 110 sends the collected medical data to email server 220 via network 230. The collected medical data may be formatted according to the defined protocol, as discussed above. A skilled artisan will appreciate that the collected medical data may constitute a confirmation or notification that embedded computing platform 110 has performed some action. Further, a skilled artisan will appreciate that the collected medical data may be empty (e.g., no notification or confirmation is desired). In one embodiment, embedded computing platform 110 may be adapted to send the data without performing analysis (i.e., send the raw collected data). In another embodiment, embedded computing platform 110 may be adapted to perform analysis prior to sending the collected medical. For example, embedded computing platform 110 may generate reports, charts, web pages, alerts, notifications, etc. that are sent in lieu of or along with the collected medical data. In yet another embodiment, embedded computing platform 110 may be adapted to generate medical images that are to be sent. For instance, embedded computing platform 110 may be configured to generate medical images using the Digital Imaging and Communications In Medicine (DICOM) format. DICOM was established in 1992 and is the standard for exchanging medical images in a digital format. These images can then be sent to email server 220. A skilled artisan will appreciate that medical images of any format may be generated in embodiments of the present invention. Further, in the preferred embodiment, embedded computing platform 110 emails the collected medical data, analysis, or images to email server 220 using the SMTP or IMAP protocols. A skilled artisan would appreciate that embedded computing platform 110 may send the medical data, analysis, or images to email server 220 also by using the protocols discussed above.

Figure 5:
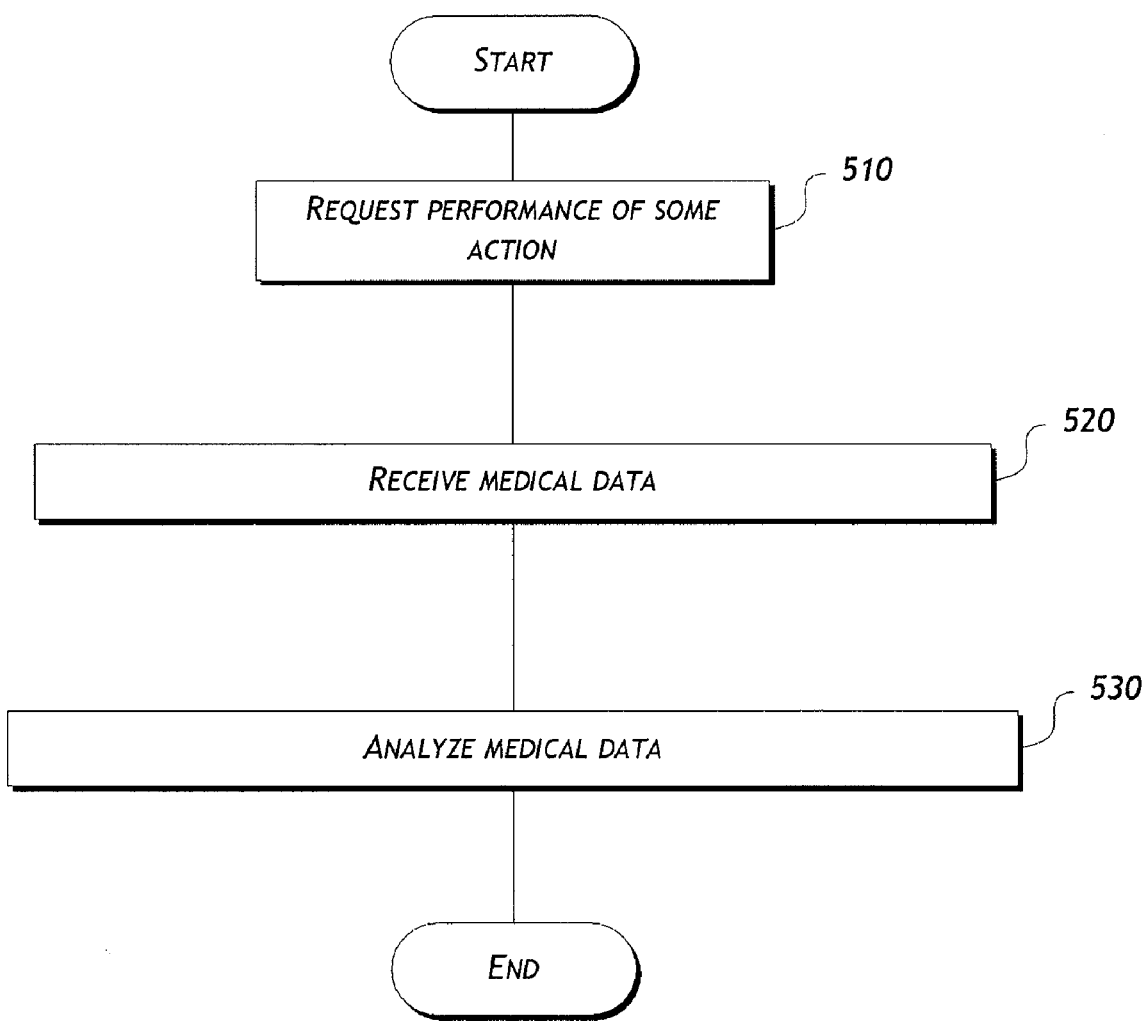
FIG. 5 illustrates a sequence of steps that may be performed by the healthcare provider system of FIG. 1, in accordance with one embodiment of the invention.

FIG. 5 illustrates a flowchart of an exemplary process by which a healthcare provider system 210, and particularly the provider computing platform 211 (FIG. 3) of such a system, requests and receives medical data in some embodiments of the present invention. Although the steps of the communication process are described as being performed in a particular order, one skilled in the art will appreciate that these steps may be performed in a modified or different order, or in an embodiment utilizing less than all of the steps described below. Further, one or more of the steps in FIG. 5 may be performed concurrently or in parallel.

First, as discussed above, provider computing platform 211 requests performance of some action (Step 510). In a preferred embodiment, the healthcare provider submits the request using a web page, and the request is transmitted to email server 220 over the Internet. The web page may be a dedicated web page for a healthcare provider program. Special log-ins may also be provided such that only members can submit requests. A skilled artisan will appreciate that the healthcare provider can input information regarding the request using any known input mechanism provided by one or more web pages or other user interface, such as pull-down menus, text boxes, selection boxes, hyperlinks, and the like. Further, a skilled artisan will appreciate that the request may also be inputted by use of a dedicated software program, application, device, etc. Moreover, the request may be formatted according to the defined protocol, as discussed above. For example, once a human operator specifies the target medical device and the type of data to be collected, application software may transform these selections into an appropriately formatted and addressed email message that can be interpreted by the medical device 100. In one embodiment, the application software is a web-based application hosted on a web application server (see FIG. 7B).

The request from the healthcare provider is then sent to email server 220 over network 230. In the preferred embodiment, the requests are sent as emails using the SMTP or IMAP protocols. In an alternate embodiment, provider computing platform 211 automatically sends a request for performance of some action without waiting for a request from the healthcare provider. In this embodiment, provider computing platform 211 can be configured to send requests to medical device 100 at predetermined intervals (e.g., daily, weekly, monthly, etc.). Moreover, if the healthcare provider is not already registered, the healthcare provider may also register with the system at this point, and may be given a membership ID and/or password. Information supplied by the healthcare provider during and after registration is maintained in patient database 221. Further, a skilled artisan will appreciate that a variety of other protocols could be used in embodiments of the present invention. For example, FTP, FTPS, SSH, HTTP, HTTPS, VOIP, GPS, CDMA, GSM, etc. may be used.

Next, provider computing platform 211 receives the requested medical data (Step 520) from email server 220, which receives the collected medical data from medical device 100. In the preferred embodiment, provider computing platform 211 receives the medical data as an email from email server 220 using the POP protocol. Provider computing platform 211 may, in one embodiment, periodically check or request email server 220 to send any emails or medical data that are to be sent to provider computing platform 211. In another embodiment, email server 220 sends emails or medical data directly to provider computing platform 211 without waiting for a request. That is, in such an embodiment, provider computing platform 211 does not periodically request or check for emails or medical data but receives the emails or medical data directly from email server 220 as they are received. Moreover, in an alternative embodiment, email server 220 does not send all the data to provider computing platform 211. Email server 220 stores the received medical data and sends a notification to provider computing platform 211 that medical data has been received. The provider computing platform 211 may then provide direct access to the medical data stored at email server 220 or may temporarily download a copy of the medical data as desired. A skilled artisan would appreciate that many modifications of the above are possible in embodiments of the present invention. For instance, provider computing platform 211 after temporarily downloading a copy of the medical data can request that email server 220 delete its copy of the medical data or the deletion can occur automatically.

In addition, in one embodiment, healthcare provider system 210 comprises an application server and a client device. In this embodiment, provider computing platform 211 is part of the application server and the application server can be located inside or outside the medical institution. As such, email server 220 sends any medical data to application server. Then application server analyzes the medical data (see step 530 below) and sends client device a notification (discussed below). Alternatively, application server can just store and analyze the received medical data without sending a notification to the client device such that the client device can access the data at any time desired. In another embodiment, healthcare provider system 210 comprises only a client device. In this embodiment, there is no application server and email server 220 sends any medical data to the client device directly. As such, the client device analyses the medical data (see step 530 below). Further, a skilled artisan would appreciate that provider computing platform 211 may receive the medical data from email server 220 also by using the various protocols discussed above.

The received medical data is then analyzed (Step 530). As part of this step, a healthcare provider reviews the received medical data. A skilled artisan will appreciate that the received medical data may also be parsed based on the defined protocol, as discussed above. In the embodiment including the application server, the application server receives the medical data from email server 220 and analyzes the data. The application server may create reports, charts, alerts, web pages, etc. for viewing by the healthcare provider. The reports, alerts, charts, web pages, etc. may relate to the status of medical device 100, status of patients connected to medical device 100, malfunctions associated with medical device 100, etc. The application server also may also create a webpage which would enable the viewing of, and alteration to the functions and performance parameters of medical device 100. After the application server has analyzed the medical data, a notification can be sent to a client device associated with a healthcare provider. The notification notifies the healthcare provider that medical data has been received and analyzed. The notification can be sent to device, such as a mobile phone, pager, personal digital assistant, computer, or the like, associated with a healthcare provider. In the embodiment where the analysis is performed by medical device 100, the application server can send the notification without performing the analysis. Subsequently, the healthcare provider can access the medical data. For instance, the healthcare provider may access a secure web page provided by the application server to view any reports, charts, alerts, etc. that were generated in response to the received medical data. Alternatively, the application server can store the received medical data and the analysis without sending a notification to the client device. In that case, the client device can access the data and analysis as discussed above when desired.

In the embodiment, where there is no application server, the client device performs the analysis discussed above. In this embodiment, the client device alerts the healthcare provider directly that medical data has been received and analyzed. In the embodiment where the analysis is performed by medical device 100, the client can alert the healthcare provider without performing the analysis. The healthcare provider then can access the analyzed medical data via the client device. Alternatively, the client device may send a notification to a device, such as a mobile phone, pager, personal digital assistant associated with the healthcare provider and then the healthcare can access the analyzed medical data via the client device.

Figure 6:
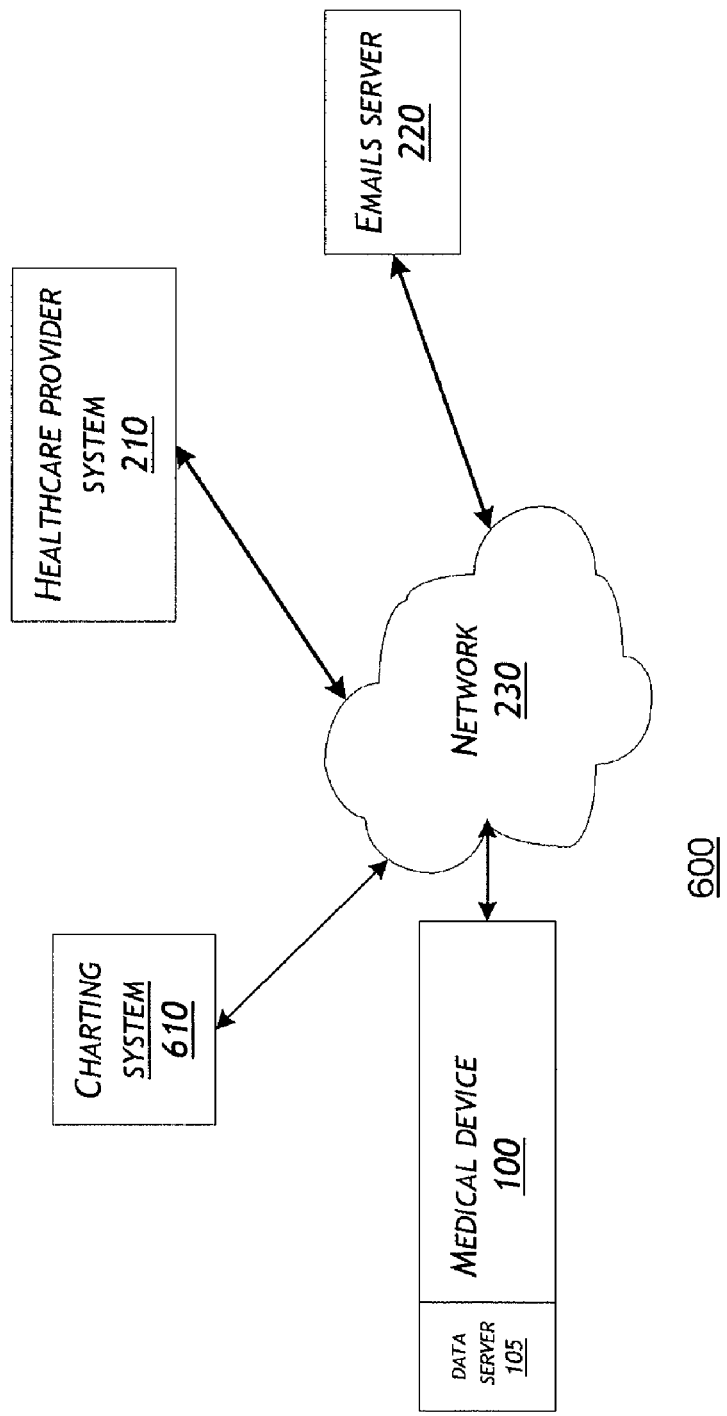
FIG. 6 is a block diagram of the system according to another embodiment.

FIG. 6 illustrates an exemplary system environment 600 for providing medical charting in some embodiments of the present invention. Similar to system 200 above in FIG. 1, system 600 may comprise multiple computer systems, such as a, a healthcare provider system 210, a medical device 100 containing a data sever 105, and an email server 220. In addition, system 600 contains a charting system 610. These various components may be connected and communicate with one another through any suitable network 230, including the Internet.

Charting system 610 is maintained by a medical institution. Charting system 610 is used by a medical institution to chart medical data collected from patients. One example of a charting system is Clinivision MPC Software that allows for the download of data from the Puritan Bennett® Ventilators directly to the charting device computer. The ventilator data is automatically integrated into the patient chart report, and users can create ventilator flow sheet reports.

However, one problem with current charting systems, is that medical device 100 must be configured to output data in a specified format so that the medical data can properly be processed by the charting system. For example, the Puritan Bennett ventilators, discussed above, must be configured to output medical data in a specified format that can be processed by the Clinivision charting software. As such, if the charting software is modified or a different charting software product is used, medical device 100 would have to be reconfigured to output medical data in a different format. This can be done by replacing medical device 100 with a different medical device or manually updating the functioning of medical device 100 by uploading a different version of the software that enables outputting the medical data in a different format. This can be troublesome if multiple medical devices have been installed because multiple medical devices may have to be replaced or updated manually.

In one embodiment, medical device 100 may be re-configured to output medical data in a different format electronically. Similar to the discussions above, medical device 100 is configured to communicate with email server 220. Email server 220 is configured to communicate with healthcare provider system 210 which is configured to communicate with charting system 610. As such, medical device 100 can be configured to output medical data in a standard format to email server 220. Then when the medical data is communicated to healthcare provider system 210, healthcare provider system 210 can be adapted to format the received medical data in a specified format and transfer the formatted medical data to charting system 610 such that charting system 610 can process the medical data. This embodiment enables the installation of a different charting program without re-configuring medical device 100. Medical device 100 can still communicate medical data in a standard format and healthcare provider system 210 can be reconfigured to format the medical data in a different format as may be needed by the different charting program.

To enable proper reformatting of the received medical data, healthcare provider system 210 can be adapted to map the received medical data in a standard format to medical data in a specified format for charting system 610. That is, healthcare provider system 210 may have a mapping table that associates medical data in the standard format to the related variables, fields, or function calls of charting system 610. A skilled artisan will appreciate that this embodiment will work if healthcare provider system 210 includes an application server or does not include an application server, as discussed above. If healthcare provider system 210 includes an application server, then application server can be configured to re-format the medical data as needed. If healthcare provider system 210 does not include an application server, then the client device can be configured to re-format the data and transfer the data to charting system 610. A skilled artisan will also appreciate that the standard format can be any format desired, even a format that can be directly processed by a particular charting system.

In another embodiment, medical device 100 can be updated to output medical data in a specified format. For example, the ventilators, as discussed above, that output medical data in a specified format for processing by the Clinivision charting software can be updated. In this embodiment, as discussed above, medical device 100 can be configured to receive a request from email server 220. In this embodiment, the request may include a software update for medical device 100. This software update would configure medical device 100 to output the medical data in a different format. A skilled artisan will appreciate that similar software updates can also be sent to healthcare provider system 210 in some embodiments of the present invention. For example, if healthcare provider system 210 includes an application server and a new charting program is now being used, a software update can be sent to the application server to provide mapping of medical data to the format needed for the new charting program. Similar updating can also be provided if healthcare provider system 210 does not include an application server and includes only a client device.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors. The code modules may be stored in any type of computer-readable medium or other computer storage device. Some or all of the methods may alternatively be embodied in specialized computer hardware. In addition, the components referred to herein may be implemented in hardware, software, firmware, or a combination thereof.

The disclosed features may be implemented in various environments, including computer-based environments, such as personal computers, workstations, servers, laptops, personal digital assistants (PDAs), mobile phones, handheld devices, and other computing devices, workstation, networked and other computing-based environments with one or more customers. The present invention, however, is not limited to such examples and embodiments of the invention may be implemented with other platforms and in other environments.

By way of example, some embodiments of the invention may be implemented using conventional personal computers (PCs), desktops, hand-held devices, multiprocessor computers, pen computers, microprocessor-based or programmable customer electronics devices, minicomputers, mainframe computers, personal mobile computing devices, mobile phones, portable or stationary personal computers, palmtop computers or the like. As used herein, the term "computing system" is intended to encompass a single computer or computing device, and is also intended to encompass a collection of computers or computing devices that interact with each other (e.g., over a network). The term "server" is intended to encompass any computing system that responds (or is programmed or configured to respond) to requests by sending or "serving" information. The term "node" is intended to encompass a computing system that is addressable on a network.

The storage media referred to herein symbolize elements that temporarily or permanently store data and instructions. Although storage functions may be provided as part of a computer, memory functions can also be implemented in a network, processors (e.g., cache, register), or elsewhere. Various types of storage mediums can be used to implement features of the invention, such as a read-only memory (ROM), a random access memory (RAM), or a memory with other access options. Further, memory functions may be physically implemented by computer-readable media, such as, for example: (a) magnetic media, like a hard disk, a floppy disk, a magnetic disk, a tape, or a cassette tape; (b) optical media, like an optical disk (e.g., a CD-ROM), or a digital versatile disk (DVD); (c) semiconductor media, like DRAM, SRAM, EPROM, EEPROM, memory stick, and/or by any other media, like paper.

Some embodiments of the invention may also include computer program products that are stored in a computer-readable medium or transmitted using a carrier, such as an electronic carrier signal communicated across a network between computers or other devices. In addition to transmitting carrier signals, network environments may be provided to link or connect components in the disclosed systems. Networking environments are commonplace in offices, enterprise-wide computer networks, intranets and the Internet (i.e., the World Wide Web). The network may be a wired or a wireless network. To name a few network implementations, the network may be, for example, a local area network (LAN), a wide area network (WAN), a public switched telephone network (PSTN), an Integrated Services Digital Network (ISDN), an infrared (IR) link, a radio link, such as a Universal Mobile Telecommunications System (UMTS), Global System for Mobile Communication (GSM), Code Division Multiple Access (CDMA), or a satellite link.

Transmission protocols and data formats are also known, such as, for example transmission control protocol/internet protocol (TCP/IP), hyper text transfer protocol (HTTP), secure HTTP, wireless application protocol, unique resource locator (URL), unique resource identifier (URI), hyper text markup language (HTML), extensible markup language (XML), extensible hyper text markup language (XHTML), wireless application markup language (WML), Standard Generalized Markup Language (SGML), etc. Such features may be utilized to implement some embodiments of the present invention, as disclosed herein.

Figure 7:
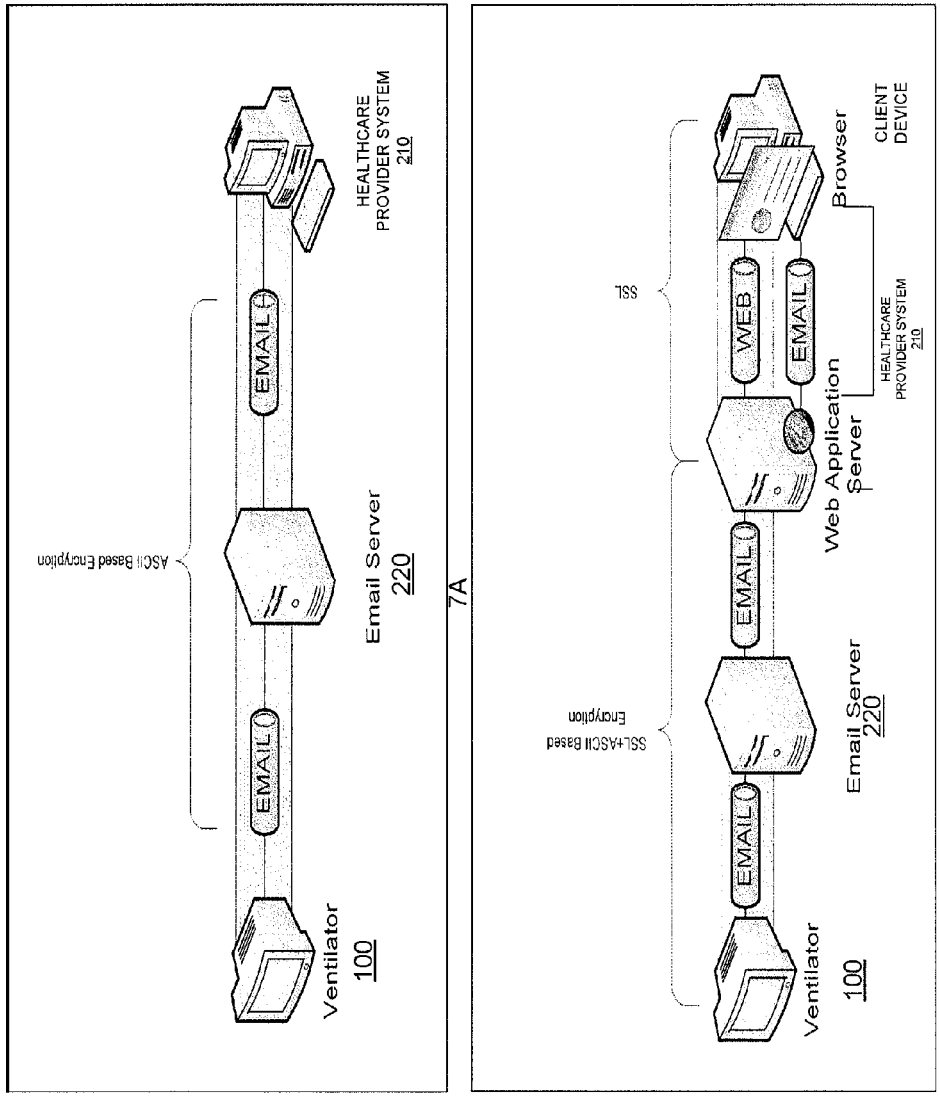
FIG. 7 illustrates one example of architecture for encryption, in accordance with one embodiment of the invention.

Moreover, to comply with HIPAA, data may be communicated in embodiments of the present invention using known encryption and decryption techniques. For example, FIG. 7 shows an exemplary encryption system for the preferred embodiment of the present invention. As shown in FIG. 7 (7A and 7B), communication from medical device 100 (e.g., ventilator) to email server 220 and communications from email server 220 and healthcare provider system 210 may be encrypted using the secure socket level (SSL) protocol. This type of encryption can be used in both embodiments relating to healthcare provider system 210. That is SSL can be used if healthcare provider system 210 includes only a client device, as shown in FIG. 7A, or if healthcare provider system 210 includes an application server and a client device, as shown if FIG. 7B. In the embodiment with the application server, as shown in FIG. 7B, SSL may also be used in communications between the application server and the client device.

Further, as also shown in FIG. 7, on top of the SSL level, all communication from and to medical device 100 are protected ASCII based security measures. In one embodiment, three layers of ASCII based security based measures may be used. The first layer may relate to cryptographic hash functions, such as MD5. The second level may relate to data blocking and stuffing. The third level may relate to private-key stream ciphering. Modifications and variations of these layers are possible in embodiments of the present invention. Additionally, a skilled artisan will appreciate that a variety of other encryption algorithms may be used in embodiments of the present invention.

In the particular embodiment shown in FIG. 7B, the application software which runs on the web application server is responsible for at least the following tasks: (1) transforming user selections made via an Internet-connected web browser and a web page into an appropriately formatted request message, such as an email, to send to the designated medical device 100; (2) sending this request message via the email server 220 to the medical device 100; (3) receiving the corresponding reply message, such as an email, generated by the medical device 100, and parsing this reply message to extract the requested data; (4) storing the extracted data in a database in association with the request message and the healthcare entity that generated the request, and (5) making this data, and other collected data, available via web-based interface.

It should be emphasized that many variations and modifications may be made to the above-described embodiments, the elements of which are to be understood as being among other acceptable examples. All such modifications and variations are intended to be included herein within the scope of this disclosure. Further, nothing in the foregoing disclosure is intended to imply that any particular component, characteristic or process step is essential.

What is claimed is:

1. A system, comprising:
a medical system operative to monitor a patient and comprises at least one medical device; and
a computing system embedded in the medical system, said computing system operative to receive commands over a network from a node external to the medical system, and operative to respond to at least some of said commands by generating, and sending over said network, email messages that include data obtained from monitoring the patient;
wherein three layers of ASCII based security based measures are used to communicate over the network: the first layer relating to cryptographic hash functions; the second level relating to data blocking and stuffing; the third level relating to private-key stream ciphering.

2. The system of claim 1, wherein the at least one medical device is a ventilator.

3. The system of claim 1, wherein the medical system is located within a medical institution.

4. The system of claim 3, wherein the node is located outside the medical institution.

5. The system of claim 1, wherein at least one of the commands comprises a request to perform an action that relates to configuring at least one setting associated with the medical system.

6. The system of claim 1, wherein the commands are received as email messages addressed to an email address associated with the medical system.

7. A method performed by a medical device, the method comprising:
by execution of instructions by the medical device:
performing a requested action;
generating a response dependent upon the requested action; and
sending the generated response on a network from the medical device as an email message;
wherein three layers of ASCII based security based measures are used to communicate over the network: the first layer relating to cryptographic hash functions;

the second level relating to data blocking and stuffing; the third level relating to private-key stream ciphering.

8. The method of claim 7, wherein the medical device is a ventilator.

9. The method of claim 7, wherein the medical device is located within a medical institution.

10. The method of claim 9, wherein the requested action is received from an email server that is located outside the medical institution.

11. The method of claim 7, wherein the requested action comprises configuring at least one setting associated with the medical device.

12. The method of claim 7, wherein communication with the medical device is limited by a firewall.

13. The method of claim 7, wherein the requested action is performed after receiving a request to perform the action over the network.

14. The method of claim 7, wherein the email message is sent by the medical device using a Simple Mail Transfer Protocol.

15. The method of claim 7, wherein the requested action is received as an email message addressed to an email address associated with the medical device.

16. A computer-implemented method of communicating with a medical device over a network, the method comprising:
receiving over the network from an email server, by the medical device, a request to perform an action; and
performing, by the medical device, the requested action;
wherein the request is received as an email message, and the medical device comprises computer hardware; and
wherein three layers of ASCII based security based measures are used to communicate over the network: the first layer relating to cryptographic hash functions; the second level relating to data blocking and stuffing; the third level relating to private-key stream ciphering.

17. The method of claim 16, wherein the medical device is a ventilator.

18. The method of claim 16, wherein the medical device is located within a medical institution.

19. The method of claim 18, wherein the email server is located outside the medical institution.

20. The method of claim 16, wherein the requested action comprises configuring at least one setting associated with the medical device.

21. The method of claim 16, wherein communication with the medical device is limited by a firewall.

22. The method of claim 16, further comprising sending an email response to the email server after performing the requested action.

23. A server system configured to communicate with a medical system over a network, the server system comprising:
a data storage system configured to store medical data received from the medical system, the medical system comprising at least one medical device; and
a server programmed via executable instructions to:
send an email request message over the network to an email server, the request message requesting the medical system to perform an action;
receive a response from the email server dependent upon the requested action, the response including medical data collected by the medical system; and
store the medical data in the data storage system;
wherein the response is received as an email message and the server comprises computer hardware; and
wherein three layers of ASCII based security based measures are used to communicate over the network: the first layer relating to cryptographic hash functions; the second level relating to data blocking and stuffing; the third level relating to private-key stream ciphering.

* * * * *